(12) United States Patent
Mi et al.

(10) Patent No.: US 11,504,021 B1
(45) Date of Patent: Nov. 22, 2022

(54) METHOD FOR DETECTING TUMOR TISSUE BOUNDARIES OR TUMOR STROMAL CELL DISTRIBUTION RANGE

(71) Applicant: Shanghai Jiao Tong University School of Medicine, Shanghai (CN)

(72) Inventors: Jun Mi, Shanghai (CN); Jiangmin Zhao, Shanghai (CN); Yazhi Xing, Shanghai (CN); Yongbin Wang, Shanghai (CN); Jinliang Wu, Shanghai (CN); Bocheng Wang, Shanghai (CN)

(73) Assignee: SHANGHAI JIAO TONG UNIVERSITY SCHOOL OF MEDICINE, Shanghai (CN)

( * ) Notice: Subject to any disclaimer, the term of this patent is extended or adjusted under 35 U.S.C. 154(b) by 945 days.

(21) Appl. No.: 16/321,535

(22) PCT Filed: Jun. 9, 2017

(86) PCT No.: PCT/CN2017/087780
§ 371 (c)(1),
(2) Date: Aug. 23, 2019

(87) PCT Pub. No.: WO2018/019038
PCT Pub. Date: Feb. 1, 2018

(30) Foreign Application Priority Data

Jul. 29, 2016 (CN) .......................... 201610615329.8

(51) Int. Cl.
*A61B 5/055* (2006.01)
*A61B 5/00* (2006.01)
(Continued)

(52) U.S. Cl.
CPC ............ *A61B 5/055* (2013.01); *A61B 5/4866* (2013.01); *A61B 6/5217* (2013.01); *G01R 33/246* (2013.01); *G01R 33/44* (2013.01)

(58) Field of Classification Search
None
See application file for complete search history.

(56) References Cited

U.S. PATENT DOCUMENTS 9,664,760 B2 * 5/2017 James ................ G01R 33/4835
10,827,945 B2 * 11/2020 Gillies ............... A61B 5/14539
(Continued)

FOREIGN PATENT DOCUMENTS

CN 104825394 A 8/2015
WO WO-2015138385 A1 * 9/2015 ........... A61B 5/0263

OTHER PUBLICATIONS

Quan, et al., "Application of Multivoxel MR Spectroscopy Imaging in the Diagnosis of Glioma", Chinese Journal of Radiology, vol. 39, No. 11, pp. 1193-1194, (Nov. 2005) (English Abstract Only).
(Continued)

*Primary Examiner* — Rodney E Fuller
(74) *Attorney, Agent, or Firm* — Panitch Schwarze Belisario & Nadel LLP

(57) ABSTRACT

A method for detecting tumor tissue boundaries or a tumor stromal cell distribution range, more specifically, a diagnostic or non-diagnostic method for determining the boundaries of a tumor tissue; the boundaries of the tumor tissue are determined by means of determining the boundaries of the tumor stromal cells in the tumor tissue. The present method can more accurately determine the boundaries of tumor tissue, which serves to more accurately instruct the treatment of tumors, especially with respect to surgical treatment.

4 Claims, 3 Drawing Sheets

(51) Int. Cl.
*A61B 6/00* (2006.01)
*G01R 33/44* (2006.01)
*G01R 33/24* (2006.01)

(56) References Cited

U.S. PATENT DOCUMENTS

| | | | |
|---|---|---|---|
| 11,080,897 B2* | 8/2021 | Li | G06T 7/13 |
| 2005/0041843 A1 | 2/2005 | Sawyer | |
| 2009/0176218 A1* | 7/2009 | Cheng | C12Q 1/6886 435/6.14 |
| 2013/0230224 A1* | 9/2013 | Claude | G06T 7/12 382/173 |
| 2015/0030615 A1* | 1/2015 | Derr | C12Q 1/6886 424/174.1 |
| 2017/0071496 A1* | 3/2017 | Gillies | A61B 5/7264 |
| 2018/0369422 A1* | 12/2018 | Haber | A61K 49/005 |

OTHER PUBLICATIONS

Wu, et al., "Metabolic Reprogramming of the Cancer-Associated Fibroblast and the Role thereof in the Occurrence and Development of the Cancer", Journal of Medical Research, vol. 45, No. 11, pp. 11-12, (Nov. 2016).

Tang, et al., "The Feasibility of 99mTc Labeled Glucose 99mTc-EC-DG in Tumor Imaging", Journal of Diagnostics Concepts & Practice, Vo. 4, No. 2, pp. 119-120, (Apr. 2005). (English Abstract Only).

Shen, et al., "Relation between MRS and Glioma Metabolism Boundary", Chinese Journal of Neuro-Oncology, vol. 8, No. 2, pp. 124-128, (Jun. 2010). (English Abstract Only).

Wei, et al., "Clinical Application of Multi-Voxel MRS in Astrocytoma", Journal of Practical Radiology, vol. 23, No. 5, pp. 577-580, (May 2007). (English Abstract Only).

International Search Report dated Sep. 6, 2017 in International Application No. PCT/CN2017/087780. (English Translation).

* cited by examiner

METHOD FOR DETECTING TUMOR TISSUE BOUNDARIES OR TUMOR STROMAL CELL DISTRIBUTION RANGE

CROSS-REFERENCE TO RELATED APPLICATION

This application is a Section 371 of International Application No. PCT/CN2017/087780, filed Jun. 9, 2017, which was published in the Chinese language on Feb. 1, 2018, under International Publication No. WO 2018/019038 A1, which claims priority under 35 U.S.C. § 119(b) to Application No. 201610615329.8, filed Jul. 29, 2016, the disclosures of which are incorporated herein by reference in their entirety.

TECHNICAL FIELD

The present invention relates to the field of diagnosis, and in particular to a method for detecting a tumor tissue boundary or a tumor stromal cell distribution range.

BACKGROUND

The main reason for the low 5-year survival rate of cancer patients is local invasion and distant metastasis of tumors. Tumor tissue includes not only tumor cells, but also a large number of tumor stroma and tumor stromal cells. A retrospective study of the incidence, clinical stage, and molecular characteristics of 282 patients with oral squamous cell carcinoma (OSCC) by Marsh et al. showed that tumor stromal cells, rather than tumor cells, determined the length of lifetime of patients.

Magnetic resonance spectroscopy (MRS) is a detecting method as a diagnostic means by using the magnetic properties of an atomic nucleus containing an odd proton in vivo and applying a magnetic field for magnetization and vibration, and to generate a magnetic resonance signal, and then converting it into a frequency (spectrum) by a Fourier formula. The technology has been developed on the basis of conventional MRI technology and can reflect information on lesions in the body or in the human body at the molecular level.

However, due to the low accuracy, MRS technology has not been applied in clinical medicine. Accordingly, the present invention is an attempt to apply MRS technology to the detection of tumor distribution ranges and to develop a more accurate diagnostic method for determining tumor tissue boundaries.

SUMMARY OF THE INVENTION

The object of the present invention is to provide a more accurate diagnostic method for determining tumor tissue boundaries.

Another object of the present invention is to provide a more accurate diagnostic method for determining the boundaries of tumor stromal cells in tumor tissues.

In the first aspect of the present invention, it provides a diagnostic or non-diagnostic method of determining tumor tissue boundaries, the method determines a boundary of a tumor tissue by determining a boundary of a tumor stromal cell distribution in the tumor tissue.

In another preferred embodiment, the method determines the boundaries of the tumor tissue by detecting the distribution ranges of tumor-associated fibroblast (CAF) cells, and/or tumor-associated macrophages (TAM) in tumor stromal cells.

In another preferred embodiment, the tumor tissue comprises all solid tumors.

In another preferred embodiment, the tumor tissue is selected from the group consisting of lung cancer, liver cancer, gastric cancer, breast cancer, cervical cancer, tongue cancer, submandibular cancer, and a combination thereof.

In another preferred embodiment, the method determines the distribution ranges of tumor tissues by detecting the amount of a specific metabolic factor in the tumor stromal cells.

In another preferred embodiment, the specific metabolic factor is selected from the group consisting of lactic acid, pyroglutamic acid, a ketone body (such as acetoacetic acid, β-hydroxybutyric acid, or acetone), glucose, and a combination thereof.

In another preferred embodiment, the method for detecting the content of a specific metabolic factor in the tumor stromal cells comprises one or more selected from the group consisting of a multi-voxel 1H MRS method, PET-CT, and SPIO-labeled phagocytosis acid probe MRI, and a combination thereof.

In another preferred embodiment, the content of the specific metabolic factor in the tumor stromal cells is detected by the multi-voxel 1H MRS method to determine the distribution ranges of the tumor tissues as described in the second aspect of the present invention.

In the second aspect of the present invention, it provides a diagnostic or non-diagnostic method for determining stromal cell boundaries in tumor tissue, comprising the steps of:

(i) providing a tumor tissue sample or an individual as a test subject;

(ii) detecting the content of a specific metabolic factor of the tumor tissue in the test subject by a multi-voxel $^1$H MRS method;

(iii) imaging the content of the specific metabolic factor to obtain a "specific metabolic factor content-distribution image"; and (iv) determining the boundaries of stromal cells in tumor tissue based on the "specific metabolic factor content-distribution image".

In another preferred embodiment, the individual carries the tumor tissue.

In another preferred embodiment, the individual comprises a human or a non-human mammal.

In another preferred embodiment, the individual comprises a non-human mammalian model.

In another preferred embodiment, the "determining the boundaries of stromal cells in tumor tissue" is to determine the boundaries of tumor stromal cells in the tumor tissue sample.

In another preferred embodiment, the "determining the boundaries of stromal cells in tumor tissue" is to determine the boundaries of tumor stromal cells in a certain part of the individual.

In another preferred embodiment, the content distribution image of the specific metabolic factor comprises an anatomically superimposed pseudocolor image.

In another preferred embodiment, the content distribution image of the specific metabolic factor comprises a two-dimensional image, or a three-dimensional image.

In another preferred embodiment, in the step (iv), a voxel having a content of the specific metabolic factor greater than a predetermined threshold Vp is defined as a tumor tissue voxel, and/or a region in which the content of a specific metabolic factor is greater than a predetermined threshold Vp is defined as a tumor tissue region, and a boundary of the stromal cell in the tumor tissue is determined as a boundary of the tumor tissue based on the tumor tissue voxel and/or the tumor tissue region.

In another preferred embodiment, in the step (iv), the method further comprises: superimposing and/or comparing the "specific metabolic factor content-distribution image" with the MRI (Chinese) image to determine the boundary of the tumor stromal cell, i.e., is the boundary of the tumor tissue.

In another preferred embodiment, the boundary of the tumor tissue encompasses the following regions:
(a) tumor tissue regions determined only in the "specific metabolic factor content—distribution image";
(b) the region of the tumor tissue determined only in the MRI image; and
(c) tumor tissue regions determined by the overlap region of "specific metabolic factor content-distribution image" and "MRI image".

In another preferred embodiment, the specific metabolic factor is selected from the group consisting of lactic acid, pyroglutamic acid, a ketone body (such as acetoacetic acid, β-hydroxybutyric acid, or acetone), glucose, and a combination thereof.

In another preferred embodiment, the specific metabolic factor comprises lactic acid.

In another preferred embodiment, the tumor tissue comprises all solid tumors.

In another preferred embodiment, the tumor tissue is selected from the group consisting of lung cancer, liver cancer, gastric cancer, breast cancer, cervical cancer, tongue cancer, submandibular cancer, and a combination thereof.

In another preferred embodiment, in step (ii), a peak of a specific metabolic factor (e.g., lactic acid) is detected at a position of 1.32±0.2 ppm (preferably 1.32±0.1 ppm).

In another preferred embodiment, in step (ii), the specific metabolic factor content of each voxel is determined based on the height, area and/or intensity of the peak of the specific metabolic factor (e.g., lactic acid).

In another preferred embodiment, in the step (iii), the method further comprises: comparing the specific metabolic factor content V in each voxel with a predetermined specific metabolic factor threshold Vp, and determining a voxel of V≥Vp as a tumor tissue voxel, determining a voxel of V<Vp as a tumor tissue voxel.

In another preferred embodiment, in step (iii), further comprising: determining a tumor tissue region based on the determined tumor tissue voxels.

In another preferred embodiment, in the step (iii), the method further comprises: comparing the specific metabolic factor content V in each region with a predetermined specific metabolic factor threshold Vp, and determining a region of V≥Vp as a tumor tissue region, determining a voxel of V<Vp as a normal tissue region.

In another preferred embodiment, in step (iii), the imaging process comprises performing a pre-treatment selected from the group consisting of: phase correction, baseline correction, metabolite chemical shift correction.

In another preferred embodiment, the voxel size is from 1 to 100 mm$^3$, preferably from 2 to 30 mm$^3$, more preferably from 3 to 20 mm$^3$, most preferably from 5 to 10 mm$^3$.

In another preferred embodiment, in the step (iv), the method further comprises: superimposing and/or comparing the "specific metabolic factor content-distribution image" with the MRI scan image to determine the boundary of the tumor tissue.

In another preferred embodiment, a choline content-distribution image is determined by detecting a choline peak at a position of 3.2±0.2 ppm (preferably 3.2±0.1 ppm).

In another preferred embodiment, the choline content in each voxel is determined based on the height, area, and/or intensity of the choline peak.

In another preferred embodiment, the "choline content-distribution image" is a two-dimensional image, or a three-dimensional image.

In the third aspect of the present invention, it provides a device for detecting a stromal cell boundary in a tumor tissue, comprising:
(a) a multi-voxel $^1$H MRS-specific metabolic factor content detection device for detecting a specific metabolic factor content in a test subject by a multi-voxel $^1$H MRS method, thereby obtaining the specific metabolic factor content in each voxel;
(b) an imaging device for performing an imaging process based on a specific metabolic factor content in each voxel, thereby obtaining a "specific metabolic factor content-distribution image";
(c) a processing device for analyzing the "specific metabolic factor content-distribution image" to determine a boundary of a stromal cell in the tumor tissue; and
(d) a display device for displaying the "specific metabolic factor content-distribution image" and the boundary of a stromal cell in the tumor tissue.

In another preferred embodiment, the imaging device is used to perform the following imaging processing: labeling voxels having different contents of V as different colors and/or grayscales based on the specific metabolic factor content V in each voxel.

In another preferred embodiment, the processing device performs the following analysis: comparing a specific metabolic factor content V in each voxel with a predetermined specific metabolic factor threshold Vp, and determining a voxel of V≥Vp as a tumor tissue voxel, and a voxel of V<Vp is determined as a normal tissue voxel.

In the fourth aspect of the present invention, it provides a diagnostic or non-diagnostic method for determining the distribution of CAF cells in a tumor tissue, comprising the steps of:
(i) providing a tumor tissue sample or an individual as a test subject;
(ii) detecting a specific metabolic factor content in the test subject by a multi-voxel $^1$H MRS method;
(iii) imaging the specific metabolic factor content to obtain a "specific metabolic factor content-distribution image"; and
(iv) Based on the "specific metabolic factor content-distribution image", it is determined that the boundary of the tumor tissue is the boundary of the CAF cell.

In another preferred embodiment, the specific metabolic factor content distribution image comprises an anatomically superimposed pseudocolor images.

In another preferred embodiment, the specific metabolic factor is selected from the group consisting of lactic acid, pyroglutamic acid, a ketone body (such as acetoacetic acid, β-hydroxybutyric acid, or acetone), glucose, and a combination thereof.

In another preferred embodiment, the tumor tissue comprises all solid tumors.

In another preferred embodiment, the tumor tissue is selected from the group consisting of lung cancer, liver cancer, gastric cancer, breast cancer, cervical cancer, tongue cancer, submandibular cancer, and a combination thereof.

In the fifth aspect of the present invention, it provides a detection device for the distribution of peripheral CAF cells of a tumor tissue, comprising:

(a) a multi-voxel $^1$H MRS-specific metabolic factor content detection device for detecting a specific metabolic factor content in a test subject by a multi-voxel $^1$H MRS method, thereby obtaining a specific metabolic factor content in each voxel;

(b) an imaging device for performing an imaging process based on a specific metabolic factor content in each voxel, thereby obtaining a "specific metabolic factor content-distribution image";

(c) a processing device for analyzing the "specific metabolic factor content-distribution image" to determine a boundary of the tumor tissue; and (d) a display device for displaying the "specific metabolic factor content-distribution image" and the boundary of the tumor tissue, wherein the boundary of the tumor tissue is the boundary of the CAF cell.

In the sixth aspect of the present invention, it provides a use of a specific metabolic factor detecting agent selected from the group consisting of lactic acid, pyroglutamic acid, ketone bodies, glucose, and a combination thereof for preparing a test kit for the determination of tumor tissue boundaries or tumor stromal cell distribution boundaries.

In another preferred embodiment, the tumor stromal cells are selected from the group consisting of tumor associated fibroblast (CAF) cells, tumor associated macrophages (TAM), and a combination thereof.

In the seventh aspect of the present invention, it provides a use of a specific metabolic factor detecting device for preparing a detection device for the determination of tumor tissue boundaries or tumor stromal cell distribution boundaries, wherein the specific metabolic factor is selected from the group consisting of lactic acid, pyroglutamic acid, ketone body, glucose, and a combination thereof.

In another preferred embodiment, the tumor stromal cells are selected from the group consisting of tumor associated fibroblast (CAF) cells, tumor associated macrophages (TAM), and a combination thereof.

It should be understood that, within the scope of the present invention, each technical feature of the present invention described above and in the following (as examples) may be combined with each other to form a new or preferred technical solution, which is not listed here due to space limitations.

DETAILED DESCRIPTION

Figure 1:
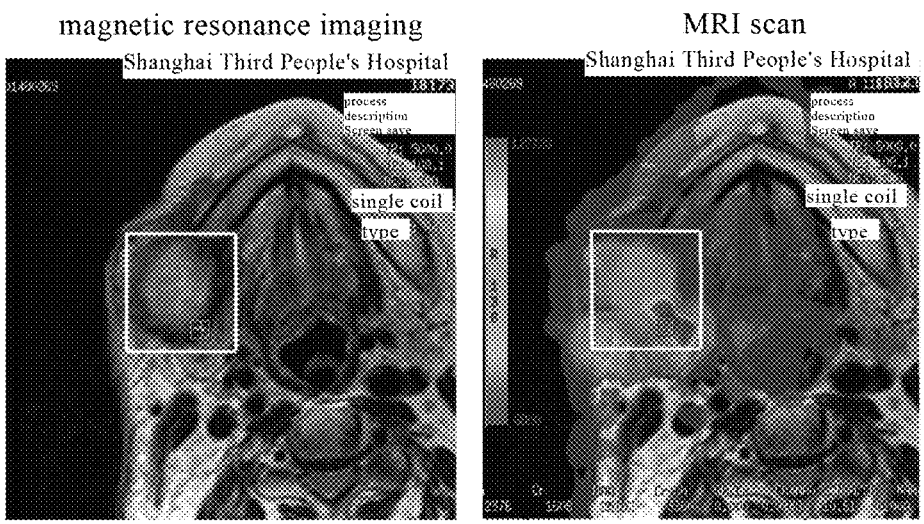
FIG. 1 shows images of the same tumor visualized in conventional MRI and images visualized in a multi-voxel 2D $^1$H MRS pseudo-color overlay. Wherein the image on the left is the MRI image of tongue cancer, and the image on the right is the image of the same tumor superimposed on the multi-voxel 2D $^1$H MRS pseudocolor images and the conventional MRI image. The red region represents a higher concentration of specific metabolic factors such as lactic acid.

After an extensive and in-depth study, the present inventors have unexpectedly discovered that the multi-voxel $^1$H MRS method combining with the anatomical superimposed pseudocolor images technology can more accurately detect the level of specific metabolic factors (such as lactic acid) of tumor tissues, thereby more accurately determining the boundaries of tumor tissues and tumor stromal cells, and can also more accurately determine the distribution boundaries of CAF cells in tumor stromal cells. On this basis, the inventors complete the present invention.

The test results of the present invention indicate that the boundaries of the tumor tissues and tumor stromal cells determined by the method of the present invention are generally irregular in shape and generally contain and are larger than the boundaries indicated by the MRI image. Therefore the method of the present invention contributes to more accurately guide the treatment (especially surgical treatment) of tumors.

The Boundary of the Tumor Tissue

Tumor tissue is composed of a tumor cell, a tumor stromal cell, and a matrix. The tumor stromal cell mainly includes a tumor-associated fibroblast (CAF), a tumor-associated immune cell, a vascular endothelial cell, a peripheral cell and the like. The distribution range of the tumor stromal cell is much larger than that of the tumor cell.

In the present invention, the boundary of the tumor tissue means that the boundary of the tumor tissue detected by the method of the present invention is very close to the real situation, and mainly refers to the distribution range of a tumor stromal cell in the periphery of the tumor tissue, such as a tumor-associated fibroblast (CAF), a tumor-associated macrophage (TAM) and the like.

In the present invention, the tumor tissue includes all solid tumors, in particular, selected from the group consisting of lung cancer, liver cancer, gastric cancer, breast cancer, cervical cancer, tongue cancer, submandibular cancer, and a combination thereof, excluding leukemia, glioma and sarcoma.

Specific Metabolic Factors in Tumor Tissues

Tumor cells and tumor-associated fibroblasts have characteristic metabolic changes—aerobic glycolysis, which have characteristic changes in nutrient uptake and metabolic intermediate production, such as a significant increase in glucose uptake and some specific metabolites such as lactic acid, pyroglutamic acid, ketone bodies and the like are produced. In the present invention, these characteristic nutrients or metabolites are collectively referred to as specific metabolic factors in tumor tissues.

CAF Cell

Carcinoma-associated fibroblast (CAF) is a class of tumor stromal cells in which the number of cells in cancerous tissues is ranked only second to tumor cells, accounting for 40%-50% of the total number of tumor tissues, it is mainly activated by fibroblasts that are stationary around cancer cells. It is well known that CAF induces tumor angiogenesis by secreting a large number of cytokines/chemokines such as basic fibroblast growth factor (bFGF), vascular endothelial growth factor (VEGF), and platelet-derived growth factor (PDGF) and the like, thereby increasing the blood supply of the tumor and promoting the growth of the tumor cells. In addition, CAF also feeds tumor cells by a large amount of lactic acid secreted by aerobic glycolysis.

In the present invention, the multi-voxel $^1$H MRS method of the present invention is combined with an anatomical superimposed pseudocolor images technique to detect the level of specific metabolic factors (such as lactic acid) of tumor tissues, thereby determining the distribution boundary of CAF cells in tumor tissues and tumor stromal cells.

Multi-Voxel

Magnetic resonance spectroscopy (MRS) is an advanced technology that enables non-invasive observation of metabolic and biochemical changes in living tissue. It is similar to the basic principle of magnetic resonance imaging, and MRS signals can be generated using for example, $^1$H, $^{31}$P, $^{13}$C, $^{19}$F, etc., and can be easily received and recognized in a specific static magnetic field. The MRS signal differs from a conventional magnetic resonance signal in that the signal distributed as a function of the time domain is transformed into a spectral line distributed in the frequency domain. Multi-voxel spectrum acquisition technology, also known as chemical shift imaging (CSI), can be divided into two-dimensional and three-dimensional multi-voxel acquisition. The advantage is that it can cover a large range in one acquisition, and obtain a plurality of voxel metabolite lines in the selected spatial distribution, so that the detection efficiency is higher than that of the single voxel. However, the multi-voxel spectrum technology has higher technical requirements for hardware and software. If the MR signal acquired without any gradient is not easy to be controlled in each voxel shape, it is also more susceptible to be impacted and polluted. The acquisition process typically needs to be repeated many times, applying a gradient in at least two directions and the image of the metabolite needs to be Fourier transformed in both the spatial and spectral fields.

Anatomical Superimposed Pseudocolor Images Technology

In the multi-voxel spectral post-processing technique, the processing of the MRS signal is more complicated than that of the conventional MRI signal. It is generally necessary to first remove the convolution in the data to calculate the signal strength of each metabolite. Usually, the time domain preprocessing, Fourier transform, frequency domain preprocessing, and spectral line quantitative calculation are used to finally obtain the calculated value of the metabolite content (concentration).

The multi-voxel spectrum signal pseudo-color image is a post-processing method for better describing the distribution concentration of signal intensity in space. The same signal distribution principle as the diagnostic grayscale is used, and based on the strength of the signal value, different colors were filled accordingly. Generally, the default setting is that the maximum upper limit of the signal domain value is dark red, and the minimum lower limit is dark blue. Therefore, when the signal value is greater than or equal to the upper limit value, the image is displayed in deep red; when the signal value is less than or equal to the lower limit value, the dark blue color is displayed on the image; and the signal intensity value of the middle part changes color with the order of red, yellow, green and blue. At the same time, it corresponds to the linear change process of the signal from large to small. Therefore, in the pseudo color map, the red concentrated area is considered to detect the concentration of a certain chemical substance, and the blue area is sparse in the concentration of the substance.

As a diagnostic positioning image paired with a pseudo color map, the acquisition level needs to be strictly consistent with the spectrum acquisition level (usually taking the horizontal transverse view without angle). Although both T1WI and T2WI can be used as anatomical localization images, T2WI is often used as a localization image in clinical practice, considering the contour display of the actual lesion and the signal difference between surrounding tissue. After the positioning map and the pseudo color map are paired and calibrated, the value range of the signal is selected (the signal outside the range is filtered and removed), and the distribution correspondent relationship between the pseudo color map and the signal intensity value can be obtained after setting the relevant calculation parameters.

Conventional MRI

The hydrogen nucleus is the most abundant and widely distributed in the human body. When it is in the main magnetic field, its hydrogen proton spin direction can be parallel to the main magnetic field. If a hydrogen nucleus receives a radio-frequency pulse with the same frequency as its spin precession, protons at a lower energy level will transition to a higher energy level, creating a resonance phenomenon. The RF pulse can deflect the direction of the magnetization vector of the hydrogen nucleus. The larger the energy is, the larger the deflection angle (such as 90° pulse, 180° pulse) will be. When the RF pulse disappears, the proton at high energy level will release the energy wave of the same frequency (i.e., MR signal) and return to the low level state, and the magnetization vector will gradually decay to zero. The conventional magnetic resonance examination sequence is a design that uses different RF pulse emission and acquisition to obtain images weighted by different properties of the material, such as T1 weighting, T2 weighting, proton weighting, and the like. Conventional magnetic resonance examination has been widely used in the examination of organs in various parts of the body. For the hydrogen proton-rich tissue, the contrast is better, but it is slightly worse for organs and lesions with more gas or calcification.

Pre-Determined Threshold Vp

Multi-voxel spectral post processing and threshold setting process:

1. Area segmentation. According to the multi-voxel, the size of the range of interest (ROI) was delimited, the segmentation is automatically performed in combination with the size of the smallest probe unit voxel. For example, in the ROI of 30 mm*30 mm, it can be divided into 5 transverse and 5 vertical and 25 minimum voxel detection units, and the signals in each unit are average filtered and retained.

2. Setting the threshold. The range of ppm values for biochemical metabolites can be set and modified, and the signals within the range are included in the measurement statistics. For a particular spectrum, the signal position of the metabolite on the horizontal axis is determined by its chemical shift, and its unit scale represents one part per million (ppm). At the same time, the spectral signal can be converted to the metabolite concentration according to the area under the measurement curve. The general default threshold settings are as follows: Choline 3.19~3.34 ppm; Creatine 2.97~3.12 ppm; N-Acetylcholine 1.96~2.13 ppm; Lipid and Lactate 0.92~1.51 ppm.

3. Signal noise. The signal range of the mixture in the interest zone is set to 0.92~3.34 ppm by default. The signal in the range is reserved, and the signal outside the range is regarded as noise.

4. Pixel baseline correction. If the test subject has slight movement or external signal interference, appropriate pixel correction can be performed, including intra-pixel displacement correction, phase correction (phasing) and baseline correction (baseline), which is usually defaulted to none.

Method for Determining Tumor Tissue Boundaries

The present invention provides a diagnostic or non-diagnostic method for determining tumor tissue boundaries, comprising the steps of:

(i) providing a tumor tissue sample or an individual as a test subject;

(ii) detecting the content of specific metabolic factors in the tumor tissue in the test subject by a multi-voxel $^1$H MRS method;

(iii) imaging the content of the specific metabolic factor to obtain a "specific metabolic factor content-distribution image";

(iv) Determining the boundary of the tumor tissue based on the "specific metabolic factor content-distribution image".

In a preferred embodiment, in the step (iv), a voxel having a content of the specific metabolic factor greater than a predetermined threshold Vp is defined as a tumor tissue voxel, and/or a region in which the content of a specific metabolic factor is greater than a predetermined threshold Vp is defined as a tumor tissue region, and a boundary of the stromal cell in the tumor tissue is determined as a boundary of the tumor tissue based on the tumor tissue voxel and/or the tumor tissue region.

In a preferred embodiment, in step (iv), further comprising: superimposing and/or comparing the "specific metabolic factor content-distribution image" with the MRI (Chinese) image to determine the boundary of the tumor tissue.

Method for Determining the Distribution Boundary of CAF Cells in Tumor Tissues

The present invention provides a method for determining the distribution of CAF cells in tumor tissue, comprising the steps of:

(i) providing a tumor tissue sample or an individual as a test subject;

(ii) detecting a specific metabolic factor content in the test subject by a multi-voxel $^1$H MRS method;

(iii) imaging the specific metabolic factor content to obtain a "specific metabolic factor content-distribution image";

(iv) based on the "specific metabolic factor content-distribution image", it is determined that the boundary of the tumor tissue is the boundary of the CAF cell.

In a preferred embodiment, the specific metabolic factor content distribution image comprises an anatomically superimposed pseudo color map.

Detection Device The present invention provides a detection device for stromal cell boundaries in tumor tissue, comprising:

(a) a multi-voxel $^1$H MRS-specific metabolic factor content detection device for detecting a specific metabolic factor content in a test subject by a multi-voxel $^1$H MRS method, thereby obtaining a specific metabolic factor content in each voxel;

(b) an imaging device for performing an imaging process based on a specific metabolic factor content in each voxel, thereby obtaining a "specific metabolic factor content-distribution image";

(c) a processing device for analyzing the "specific metabolic factor content-distribution image" to determine a boundary of stromal cells in the tumor tissue; and (d) a display device for displaying the "specific metabolic factor content-distribution image" and the boundary of stromal cells in the tumor tissue.

In addition, the present invention also provides a detection device for the distribution of peripheral CAF cells of tumor tissue, comprising:

(a) a multi-voxel $^1$H MRS-specific metabolic factor content detection device for detecting a specific metabolic factor content in a test subject by a multi-voxel $^1$H MRS method, thereby obtaining a specific metabolic factor content in each voxel;

(b) an imaging device for performing an imaging process based on a specific metabolic factor content in each voxel, thereby obtaining a "specific metabolic factor content-distribution image";

(c) a processing device for analyzing the "specific metabolic factor content-distribution image" to determine a boundary of the tumor tissue; and (d) a display device for displaying the "specific metabolic factor content-distribution image" and the boundary of the tumor tissue, wherein the boundary of the tumor tissue is the boundary of the CAF cell.

The Main Advantages of the Present Invention Include:

(1) The present invention combines the multi-voxel $^1$H MRS method with the anatomical superimposed pseudo-color map technique for the first time to detect the content of specific metabolic factors (such as lactic acid), thereby more accurately determining the distribution boundaries of tumor tissues and stromal cells in tumor tissues.

(2) Compared with the conventional MRI, the tumor tissue boundary determination method of the present invention not only shows the core tumor region, but also shows the peripheral non-core tumor region, which can more accurately reflect the distribution range of the tumor, and thus has higher accuracy.

(3) The present invention combines the multi-voxel $^1$H MRS method with the anatomical superimposed pseudo-color map technique for the first time to detect the content of specific metabolic factors (such as lactic acid), thereby more accurately determining the boundary of CAF cells in tumor tissues.

The invention is further illustrated below in conjunction with specific embodiments. It is to be understood that the examples are not intended to limit the scope of the invention. The experimental methods in the following examples which do not specify the specific conditions are usually carried out according to conventional conditions or according to the conditions recommended by the manufacturer. Percentages and parts are by weight unless otherwise stated.

Unless otherwise defined, all professional and scientific terms used herein have the same meaning as those skilled in the art. In addition, any methods and materials similar or equivalent to those described may be employed in the methods of the invention. The preferred embodiments and materials described herein are for illustrative purposes only.

Example 1

Normal Information:

An elderly woman, 81 years old, a right lower maxillofacial mass was found for more than half a year. She was treated with radiation on Aug. 14, 2015. Pathology before radiotherapy: right squamous cell carcinoma of the right lower jaw did not show vascular-lymphatic tumor thrombus visible nerve infiltration. Tumor patients were followed by routine MRI examination according to the specified protocol, and the multi-voxel lactic acid two-dimensional 1H MRSI/anatomical superimposed pseudo-color map was performed.

MRI Detection Method and Scanning Parameters:

The magnetic resonance used in the present invention was a GE signa 1.5 THD MRI superconducting magnetic resonance scanner; a head phased array coil was used for the post-processing workstation (ADW 4.4). The patient's position was supine position and the head went into firstly, so that the patient's median line was as close to the center of the coil as possible and symmetrical. MRI flat scan: after conventional magnetic resonance localization scan, the positioning phase was obtained, axial and sagittal fat suppressed T2WI scan. Scanning parameters: TE 108 ms, TR 5000 ms, layer thickness 5.0 mm, layer spacing 0 mm, FOV 24 cm, matrix 320×224, NEX=2. Spectral spectrum: After the flat image was collected, according to the position of the flat image, the SI-PRESS sequence was used for examination. The voxel was generally selected to contain part of the lesion tissue, and the surrounding non-lesional tissue should be included as much as possible. The general voxel size was about 18 mm$^3$. Usually, it was equal to or greater than the default value, TR 1000 ms, TE 35 m s, NEX=1, shimming and fat suppression before scanning. Image post-processing: Transferring the original image data to the post-processing workstation, and using the SER software in Fun ctool to process the acquired MRS data, such as phase and baseline correction, determination of chemical shift of metabolites, etc., and observing the presence of abnormal increase in lactate peak, choline peak and peak height at 1.3 ppm and 3.2 ppm, respectively.

The result is shown in FIG. 1. The results show that the boundary of the tumor includes and is larger than the MRI image area, and its true range is larger than that on the MRI image, and has no correlation with the MRI image.

A similar method to that of Example 1 is used, except that a specific metabolic factor such as pyroglutamic acid, a ketone body (such as acetoacetic acid, β-hydroxybutyric acid, or acetone) or glucose is used for the detection of the distribution boundary of right squamous cell carcinoma of the lower jaw. The results show that the content of specific metabolic factors such as pyroglutamic acid, ketone body (such as acetoacetic acid, β-hydroxybutyric acid, or acetone) or glucose was imaged, and the obtained distribution boundary of the tumor is similar to those obtained with lactic acid.

In addition, a similar method to that of Example 1 was used, except that the boundary of other tumor tissues (such as lung cancer, liver cancer, stomach cancer, breast cancer, cervical cancer, tongue cancer) was detected with lactic acid, and the results show that the content of lactic acid was imaged, the obtained distribution boundary of the tumor is similar to that of the right lower jaw squamous cell carcinoma obtained with lactic acid.

Example 2

Normal Information:

The patient is a breast cancer patient or a tongue cancer patient, regardless of gender or age, from 48 to 87 years old. The patients underwent MRI and MRS for imaging diagnosis before operation. After the operation, the core tumor boundary region was taken for CAF cell-specific marker protein FSP1 immunohistochemistry or immunofluorescence detection.

Figure 2:
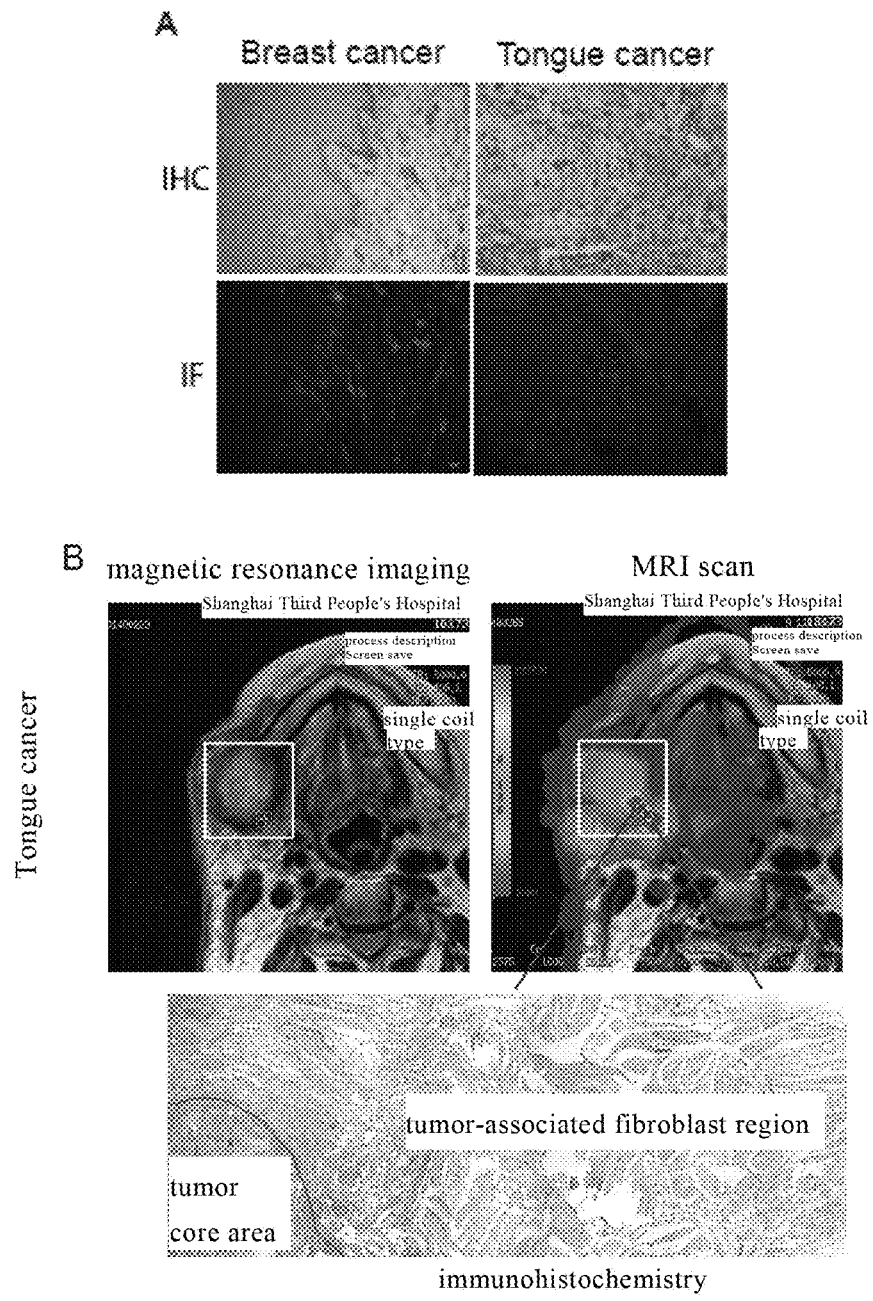
FIG. 2 shows the distribution ranges of CAF cells and the relationship between the area of highly specific metabolic factors (such as lactic acid) in tongue cancer patients and the distribution ranges of CAF cells. Figure A shows the presence of a large number of CAF cells outside the core tumor area in the border tissue of breast cancer and tongue cancer by immunohistochemistry and immunofluorescence, respectively. Figure B shows that the region of high specific metabolic factors (such as lactic acid) is mainly CAF distribution region.

The results are shown in FIGS. 2A and 2B. FIG. 2A shows that there are a large number of CAF cells outside the distribution of tumor cells in breast cancer and tongue cancer tissues. FIG. 2B shows in vivo MRS images of patients with tongue cancer (pseudo-color map) are much larger than their MRI image; the in vitro immunohistochemistry results of the corresponding sites after surgery also show that the MRS high lactic acid distribution area outside the MRI image is CAF cells.

A similar method to that of Example 2 is used, except that a specific metabolic factor such as pyroglutamic acid, a ketone body (such as acetoacetic acid, β-hydroxybutyric acid, or acetone) or glucose is used instead of lactic acid for the detection of the distribution boundary of CAF cells in breast cancer or tongue cancer. The results show that the content of specific metabolic factors such as pyroglutamic acid, ketone body (such as acetoacetic acid, β-hydroxybutyric acid, or acetone) or glucose was imaged, and the distribution boundary of the obtained CAF cells is similar to that of CAF cells of breast cancer or tongue cancer obtained with lactic acid.

Further, a similar method to that of Example 2 was used, except that the boundary of CAF cells of other tumor tissues (such as lung cancer, liver cancer, gastric cancer, cervical cancer, and submandibular cancer) was detected by lactic acid, and the results show that the content of lactic acid was imaged, the obtained distribution boundary of CAF cells of the tumor is similar to that of CAF cells of tongue or breast cancer obtained with lactic acid.

Example 3

Normal Information:

The patient is an early stage lung cancer patient who cannot be treated by surgery, no limitation for the gender and age, from 48 years old to 87 years old, traditional EBRT (external irradiation radiotherapy) or improved SBRT (three-dimensional aptamer radiotherapy) was performed respectively, the total dose of radiotherapy was the same, it was 65±5 Gy. Since 2008, a total of 96 cases had been collected, all of whom were from Shanghai Top A Hospital. All patients underwent a retrospective study to determine the time to relapse and survival.

Figure 3:
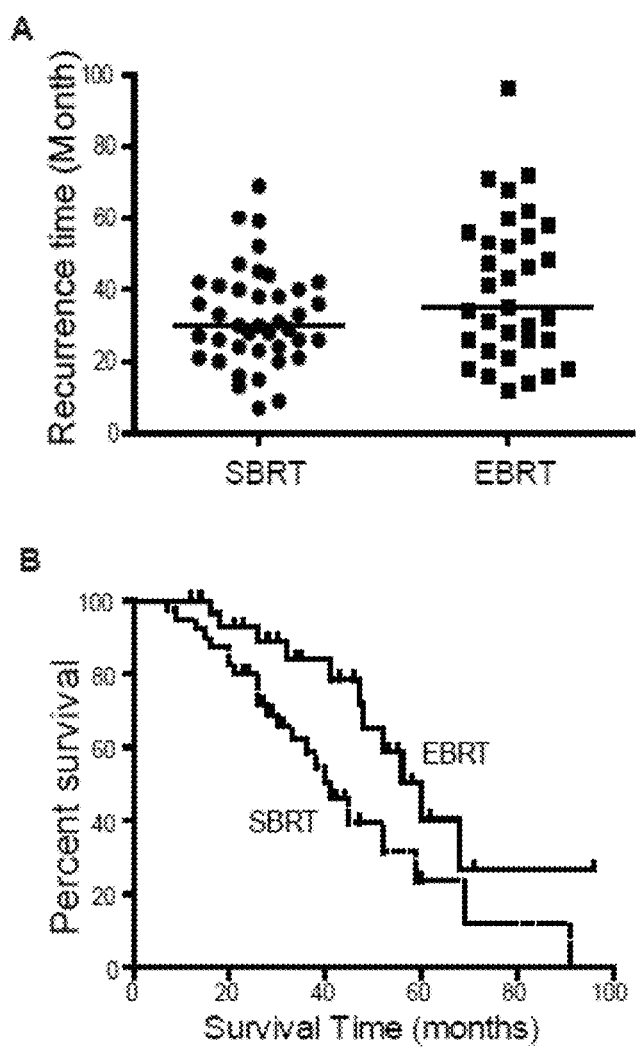
FIG. 3 shows a comparison of the time to relapse and survival after treatment with EBRT or SBRT in patients with lung cancer. Figure B shows a comparison of the time to relapse (median) of lung cancer treated with SBRT or EBRT; Figure A shows a comparison of survival time after treatment with SBRT or EBRT in patients with lung cancer.

The results are shown in FIGS. 3A and 3B. The results show that SBRT accelerates tumor recurrence relative to EBRT, and the time to recurrence (median) decreases from 36 months to 28 months, and shortens the survival of tumor patients. The survival time (median) is shortened from 56 months to 39 months.

All literatures mentioned in the present application are incorporated by reference herein, as though individually incorporated by reference. Additionally, it should be understood that after reading the above teaching, many variations and modifications may be made by the skilled in the art, and these equivalents also fall within the scope as defined by the appended claims.

The present invention provides a method for detecting a tumor tissue boundary or a tumor stromal cell distribution range, more specifically, the present invention provides a diagnostic or non-diagnostic method for determining the boundaries of a tumor tissue; the boundaries of the tumor tissue are determined by means of determining the boundaries of the tumor stromal cells in the tumor tissue. The method provided by the invention can more accurately determine the boundaries of tumor tissue, which contributes to more accurately guide the treatment (especially surgical treatment) of tumors.

The invention claimed is:

1. A diagnostic or non-diagnostic method of determining tumor tissue boundaries, comprising determining a boundary of a tumor tissue by determining a boundary of a tumor stromal cell distribution in the tumor tissue,
   wherein the method determines the boundaries of the tumor tissue by detecting the distribution ranges of tumor-associated fibroblast (CAF) cells, and/or tumor-associated macrophages (TAM) in tumor stromal cells,
   wherein the method determines the distribution ranges of tumor tissues by detecting the amount of a specific metabolic factor in the tumor stromal cells, and
   wherein the specific metabolic factor is selected from the group consisting of: lactic acid, pyroglutamic acid, ketone bodies, glucose, and a combination thereof.

2. A diagnostic or non-diagnostic method for determining stromal cell boundaries in tumor tissue, comprising the steps of:
   (i) providing a tumor tissue sample or an individual as a test subject;
   (ii) detecting the content of a specific metabolic factor of the tumor tissue in the test subject by a multi-voxel $^1$H MRS method;
   (iii) imaging the content of the specific metabolic factor to obtain a specific metabolic factor content-distribution image;
   (iv) determining the boundaries of stromal cells in tumor tissue based on the specific metabolic factor content-distribution image, and the specific metabolic factor is selected from the group consisting of: lactic acid, pyroglutamic acid, ketone bodies, glucose, and a combination thereof; wherein the boundary of the tumor tissue is determined to be the boundary of CAF cells in the tumor tissue.

3. The method of claim 2, wherein in the step (iv), a voxel having a content of the specific metabolic factor greater than a predetermined threshold Vp is defined as a tumor tissue voxel, and/or a region in which the content of a specific metabolic factor is greater than a predetermined threshold Vp is defined as a tumor tissue region, and a boundary of the stromal cell in the tumor tissue is determined as a boundary of the tumor tissue based on the tumor tissue voxel and/or the tumor tissue region.

4. A device for detecting a stromal cell boundary in a tumor tissue, comprising:
   (a) a multi-voxel $^1$H MRS-specific metabolic factor content detection device for detecting a specific metabolic factor content in a test subject by a multi-voxel $^1$H MRS method, thereby obtaining the specific metabolic factor content in each voxel;
   (b) an imaging device for performing an imaging process based on a specific metabolic factor content in each voxel, thereby obtaining a "specific metabolic factor content-distribution image";
   (c) a processing device for analyzing the "specific metabolic factor content-distribution image" to determine a boundary of a stromal cell in the tumor tissue; and
   (d) a display device for displaying the "specific metabolic factor content-distribution image" and the boundary of a stromal cell in the tumor tissue, and the specific metabolic factor is selected from the group consisting of: lactic acid, pyroglutamic acid, ketone bodies, glucose, and a combination thereof; wherein the boundary of the stromal cell in the tumor tissue is determined to be the boundary of CAF cells in the tumor tissue.

* * * * *